US006350459B1

(12) United States Patent
Suzuki et al.

(10) Patent No.: US 6,350,459 B1
(45) Date of Patent: Feb. 26, 2002

(54) SOLUBILIZED COSMETIC COMPOSITION WITH A PHARMACEUTICAL OR COSMETIC AGENT, A METHACRYLATE COPOLYMER AND A CYCLODEXTRIN

(75) Inventors: Kazuaki Suzuki; Wataru Tokue, both of Yokohama; Kenzo Ito, Kakegawa; Shoji Nishiyama, Yokohama, all of (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/101,189

(22) PCT Filed: Nov. 14, 1997

(86) PCT No.: PCT/JP97/04156

§ 371 Date: Jul. 10, 1998

§ 102(e) Date: Jul. 10, 1998

(87) PCT Pub. No.: WO98/20841

PCT Pub. Date: May 22, 1998

(30) Foreign Application Priority Data

Nov. 14, 1996 (JP) .............................................. 8-318678
Oct. 31, 1997 (JP) .............................................. 9-315979

(51) Int. Cl.⁷ .................................................. A61K 9/10
(52) U.S. Cl. ........................ 424/401; 424/78.02; 514/58
(58) Field of Search .............................. 424/401, 78.02; 514/58

(56) References Cited

U.S. PATENT DOCUMENTS

| 5,070,081 A | * 12/1991 | Majid et al. |
| 5,562,642 A | 10/1996 | Smith et al. ................. 604/289 |
| 5,643,584 A | 7/1997 | Farng et al. ................. 424/401 |
| 5,821,237 A | 10/1998 | Bissett et al. ................. 514/75 |

FOREIGN PATENT DOCUMENTS

| EP | 366154 | * 5/1990 |
| EP | 442420 | * 8/1991 |
| JP | 2-196709 | 8/1990 |
| JP | 3-157314 | 7/1991 |
| JP | 8-217628 | 8/1996 |
| WO | 90/14082 | 11/1990 |
| WO | 94/12217 | 6/1994 |
| WO | 94-21225 | * 9/1994 |

* cited by examiner

Primary Examiner—Raj Bawa
(74) Attorney, Agent, or Firm—Foley & Lardner

(57) ABSTRACT

A solubilized cosmetic composition containing an ingredient which is difficult to be dissolved in water, an alkyl-modified carboxyvinyl polymer and a hydroxyalkylated cyclodextrin so as to solubilize the ingredient difficult to be dissolved in water and in particular substantially not containing a surfactant.

4 Claims, No Drawings

SOLUBILIZED COSMETIC COMPOSITION WITH A PHARMACEUTICAL OR COSMETIC AGENT, A METHACRYLATE COPOLYMER AND A CYCLODEXTRIN

TECHNICAL FIELD

The present invention relates to a solubilized cosmetic composition, more particularly it relates to a solubilized cosmetic composition which is superior in long term stability over time, is not accompanied by a sticky feeling in use, and is superior in clarity, without substantially containing a surfactant.

BACKGROUND ART

In the past, wide use has been made of cosmetic compositions which solubilize ingredients difficult to be dissolved in water, for example, perfumes, oil-soluble medicines, oils, and the like in the form of a cosmetic water, etc. It had been considered essential to formulate a surfactant into cosmetic compositions of a type solubilizing ingredients difficult to be dissolved in water so as to ensure stability over time of the cosmetics.

In recent years, however, greater safety has been expected even in cosmetic composition. From this viewpoint, the inclusion of surfactants in cosmetic compositions has been considered a problem in some cases. Therefore, it has been proposed to obtain a solubilized cosmetic composition, without substantially using a surfactant (for example, see JP-A-2-196709).

However, such a solubilized cosmetic substantially not containing a surfactant, is not sufficiently satisfactory in long term stability over time of the solubilized state. Further, in terms of usability, there had been a tendency for an accompanying sticky feeling of use.

DISCLOSURE OF INVENTION

Accordingly, an object of the present invention is to provide a solubilized cosmetic composition, which is superior in long term stability over time, and is not accompanied by a sticky feeling in use, substantially without using a surfactant.

In accordance with the present invention, there is provided a solubilized cosmetic composition containing an ingredient which is difficult to be dissolved in water, an alkyl-modified carboxyvinyl polymer and a hydroxyalkylated cyclodextrin so as to solubilize the ingredient difficult to be dissolved in water.

BEST MODE FOR CARRYING OUT THE INVENTION

The present inventors engaged in repeated studies to solve the above-mentioned problems and found that by formulating an alkyl-modified carboxyvinyl polymer and hydroxyalkylated cyclodextrin in a cosmetic composition containing an ingredient difficult to be dissolved in water, the solubilized state was stabilized over a long period of time and the feeling in use was improved and, further, found that by formulating in a specific ratio of the ingredients, it was possible to obtain a solubilized cosmetic composition having a particularly superior clarity, whereby the present invention has been completed.

Note that, in this specification, unless otherwise indicated, "an ingredient which is difficult to be dissolved in water" will be referred to as "an ingredient difficult to be dissolved in water". Further, a "cosmetic composition obtained by solubilizing an ingredient insoluble in water" will be referred to as a "solubilized cosmetic composition", but the specific form is not questioned. Further, in the present specification, "solubilized" means the ingredient difficult to be dissolved in water dissolves to at least the solubility in water and the turbidity of the aqueous solution is decreased. Further, in the present specification, "substantially not containing a surfactant" means not containing a surfactant as a means for solubilizing the cosmetic and is not intended to positively inhibit the formulating of a surfactant in the cosmetic composition for other purposes.

The solubilized cosmetic composition according to the present invention is a solubilized cosmetic composition in which an alkyl-modified carboxyvinyl polymer and hydroxyalkylated cyclodextrin are formulated as solubilizing agents.

As the alkyl-modified carboxyvinyl polymer formulated in the solubilized cosmetic composition of the present invention, mainly an acrylate-methacrylate alkyl copolymer can be mentioned. The alkyl-modified carboxyvinyl polymer may be produced using a standard method according to the specific molecular structure. As the modifying alkyl group, a $C_{10}$ to $C_{20}$ alkyl group may be mentioned.

Further, a commercially available alkyl-modified carboxyvinyl polymer may also be formulated in the solubilized cosmetic composition of the present invention.

As such a commercially available product, it is possible, for example, to formulate, as an acrylate-methacrylate alkyl copolymer, Carbopol 1342, Pemulen TR-1, Pemulen TR-2 (each made by BF Goodrich), etc. into the solubilized cosmetic composition of the present invention.

The amount of the alkyl-modified carboxyvinyl polymer formulated into the solubilized cosmetic composition of the present invention is preferably at least 0.0001% by weight and not more than 1.0% by weight, based upon the total weight of the cosmetic composition. If considering the balance of the solubilizing power and usability, it is particularly preferable to formulate it in a range of at least 0.001% by weight to not more than 0.5% by weight, based upon the total weight of the cosmetic.

If the amount of the alkyl-modified carboxyvinyl polymer is less than 0.0001% by weight, the desired solubilization is not sufficiently achieved. Contrary to this, when the amount is more than 1.0% by weight, there is a strong tendency for an accompanying sticky feeling in use, and therefore, are not preferable.

Note that, when using a non-alkyl-modified carboxyvinyl polymer such those normally used as a thickener, for example, Carbopol 941 (made by BF Goodrich), Hiviswako 105 (made by Wako Pure Chemical Industries Ltd etc., the solubilizing power is weak and it is not possible to produce the desired solubilized cosmetic composition.

Further, the hydroxyalkylated cyclodextrin formulated in the solubilized cosmetic composition of the present invention (hereinafter sometimes abbreviated as "HACD")is a cyclodextrin known in the past as a cyclic oligosaccharide (hereinafter sometimes abbreviated as "CD")at whose hydroxy group a hydroxyalkyl group is introduced. That is, as the cyclodextrin, cyclodextrins having α-, β-, or γ-structures depending on the different number of glucoses (hereinafter sometimes abbreviated as α-CD, β-CD, and γ-CD) are known and commercially available. The hydroxyalkylated cyclodextrin formulated in the solubilized cosmetic composition of the present invention is produced by hydroxyalkylating the hydroxy group of these cyclodextrins. Note that, among the cyclodextrins serving as the base of these hydroxyalkylated cyclodextrins, normally β-CD is used, but α-CD or γ-CD may also be used as a mother nucleus. Further, it is possible to use an amylolyte containing all of these α-CD, β-CD, and γ-CD as a mother nucleus.

The replacement of the hydroxy group of the cyclodextrin with a hydroxyalkyl group may be performed using an ordinary known means (for example, see JP-A-2-196709). Further, the mole substitution degree of the hydroxyalkyl group is preferably 1 to 14.

As the hydroxyalkyl group replacing the hydroxy group, for example, substituent group such as a hydroxymethyl group, hydroxyethyl group, hydroxypropyl group, may be illustrated.

By the substitution reaction, it is possible to obtain hydroxyalkylated cyclodextrins such as hydroxymethylcyclodextrin, hydroxyethylcyclodextrin, hydroxypropylcyclodextrin, hydroxybutylcyclodextrin, dihydroxypropylcyclodextrin.

Further, among these hydroxyalkylated cyclodextrins, considering the production cost and easy production and the usability and the solubility in water of the cosmetic composition obtained by formulating the same into the solubilized cosmetic composition of the present invention, it is preferable to formulate a hydroxyethylated β-CD or hydroxypropylated β-CD in the solubilized cosmetic composition of the present invention. However, the hydroxalkylated cyclodextrin which can be formulated into the solubilized cosmetic composition of the present invention is not limited to these hydroxyalkylated cyclodextrins.

Further, these hydroxyalkylated cyclodextrins may be formulated into the solubilized cosmetic composition of the present invention alone, but mixtures thereof (mixtures suitably selected from hydroxyalkylated α-, β-, and γ-CD's substituted by various types of hydroxyalkyl groups) may also be formulated.

The amount of the above hydroxyalkylated cyclodextrin formulated into the solubilized cosmetic composition of the present invention is preferably at least 0.001% by weight to less than 5.0% by weight based upon, particularly preferably 0.01% by weight to 1.0% by weight, the total weight of the cosmetic composition.

If the amount of the hydroxyalkylated cyclodextrin formulated is less than 0.001% by weight, the desired solubilization cannot be sufficiently performed, while conversely, if more than 5.0% by weight, not only is there a strong tendency for an accompanying sticky feeling in use, but also there is a tendency for a decreasing in the stability over time.

As a typical example of an ingredient difficult to be dissolved in water, formulated into the solubilized cosmetic composition of the present invention, a perfume or a fat-soluble medicine may be mentioned.

As the fat-soluble medicine, for example, vitamin A esters such as retinol, 3-dehydroretinol, retinal, 3-dehydroretinal, rhetinic acid, 3-dehydrorhetinic acid, vitamin A acetate, vitamin A palmitate, vitamin A such as α-carotene, β-carotene, γ-carotene, β-cryptoxanthin, exinenon, and other carotenoids and xantophylls and other provitamins; vitamin D such as vitamin D2 to D7; vitamin E such as α-tocopherol, β-tocopherol, γ-tocopherol, δ-tocopherol, α-tocotriel, β-tocotriel, γ-tocotriel, δ-tocotriel, vitamin E acetate, vitamin E nicotinate, and other fat-soluble vitamins.

Further, as the fat-soluble medicines other than fat-soluble vitamins, Photosensitizing Dye No. 201, Photosensitizing Dye No. 301, stearyl glycyrrhetinate, glycyrrhetinic acid, γ-oryzanol, hinokitiol, musidine (phonetic), bisabolol, inositol, and the like may be mentioned.

These fat-soluble medicines and perfumes may, of course, be dissolved in the solubilized cosmetic composition of the present invention alone and may be dissolved in the case of any mixtures of two or more as well.

Further, the solubilized cosmetic composition of the present invention may further contain therein, in addition to the above-mentioned fat-soluble medicines, ingredients difficult to be dissolved in water generally formulated into cosmetics composition or pharmaceuticals to an extent not impairing the desired effect of the present invention.

Specifically, as an oil component, oils such as avocado oil, corn oil, olive oil, rapeseed oil, evening primrose oil, castor oil, sunflower oil, tea seed oil, rice bran oil, jojoba oil, cacao oil, palm oil, serge oil, lavender oil, squalane, squalene, tallow, Japan wax, beeswax, candelilla wax, carnauba wax, lanolin, silicone oil, fluorine oil, liquid paraffin, ceresin, vaseline, pentaerythritol ethylhexanoate, glyceryl ethylhexanoate, cetyl ethylhexanoate, glyceryl monooleate, may be mentioned. As a higher alcohol, capryl alcohol, lauryl alcohol, myristyl alcohol, cetyl alcohol, and the like may be mentioned. As a sterol, cholesterol, phytosterol, etc. may be mentioned. As a higher fatty acid, capric acid, lauric acid, myristic acid, palmitic acid, stearic acid, behenic acid, lanolin fatty acid, linoleic acid, linolenic acid, etc. may be mentioned. As UV absorbers, p-aminobenzoic acid, homomenthyl-7N-acetyl anthranilate, butylmethoxybenzoylmethane, glyceryl diparamethoxycinnamate-mono-2-ethylhexanoate, aminosalicylate, octylcinnamate, 2,4-dehydroxybenzophenone, oxybenzone, 4-tert-butyl-4'-methoxydibenzoylmethane, 2-ethylhexyl p-methoxycinnamate, sodium hydroxymethoxybenzophenone sulfonate, etc. may be mentioned. As an antibiotic preservative, p-oxybenzoate alkylester (ethylparaben, butylparaben, etc.), and hexachlorophene, etc. may be mentioned.

The amount of the ingredient difficult to be dissolved in water, formulated in the solubilized cosmetic composition of the present invention depends mainly on the amount of the alkyl-modified carboxyvinyl polymer. That is, the formulation of at least 10 times the above alkyl-modified carboxyvinyl polymer by weight with respect to the ingredient difficult to be dissolved in water is preferable in achieving the desired effect of the present invention.

That is, if the amount of the alkyl-modified carboxyvinyl polymer is more than 10 times the ingredient difficult to be dissolved in water, in particular the clarity of the solubilized cosmetic composition of the present invention is improved and superior effects are achieved in both the stability over time and stability immediately after preparation of the product.

The solubilized cosmetic composition of the present invention may contain therein, in addition to the water and the ingredient difficult to be dissolved in water, medicines and bases easily dissolvable in water which are generally formulated into cosmetics in the past to an extent not impairing the effect desired according to the present invention.

The form of the solubilized cosmetic composition of the present invention is not particularly limited so long as the cosmetic composition is one which requires solubilization of an ingredient insoluble in water by nature. For example, the present invention may be applied to a cosmetic water, tonic, clear gel, two-layer water-powder cosmetic, etc.

Specific formulations of the solubilized cosmetic composition of the present invention are given in the following Examples.

EXAMPLES

The present invention will now be explained in detail with reference to Examples, but the present invention is of course not limited to these Examples. Note that the following amounts are expressed as percents by weight based upon the total weight of the cosmetic composition unless otherwise indicated.

The methods of evaluation of the solubilized cosmetic composition according to the present invention used in the Examples were as follows:

Method of Evaluation of Turbidity

The turbidity of the cosmetic composition was measured by a Poic integrated bulb type turbidimeter (blackboard method). The lower the turbidity, the higher the clarity. The higher the turbidity, the cloudier the cosmetic composition. Note that the turbidity is preferably in the range of 1 to 30, in the solubilized cosmetic composition of the present invention, more preferably a range of 1 to 20.

Methods for Evaluation of Stability
(1) Evaluation Method 1

The stability of the solubilized cosmetic composition was evaluated by visually observing the state of the solubilized cosmetic composition being evaluated immediately after being prepared at room temperature to determine the stability.

Criteria for Evaluation of Stability

○: Clear

Δ: Semiclear

×: Clear separation of oil observed (2) Evaluation Method 2

The stability over time of the solubilized cosmetic composition was evaluated by visually observing the state after the solubilized cosmetic composition being evaluated was allowed to stand at 0° C., room temperature, or 50° C. for one month to determine the long term stability.

Criteria for Evaluation of Stability Over Time
(Overall Evaluation for Three Above Temperature Groups)

⊙: No separation of oil observed at all

○: Almost no separation of oil observed

Δ: Slight separation of oil observed

×: Clear separation of oil observed

Method of Evaluation of Usability

A panel of 10 women (healthy women) was made to use the cosmetic and evaluate its usability.

Criteria for Evaluation of Usability

○: Not sticky (at least 7 women evaluated the cosmetic as not sticky)

Δ: Felt slightly sticky (4 to 6 women evaluated the cosmetic as not sticky)

×: Felt sticky (not more than 3 women evaluated the cosmetic as not sticky)

Test Examples 1 to 5

The cosmetic waters having the formulations shown in Table 1 were prepared by adding the alcohol phases to the aqueous phases and were evaluated as to the turbidity, stability immediately after preparation, and stability over time of the cosmetic waters.

TABLE 1

| Ingredient | Test Ex. 1 | Test Ex. 2 | Test Ex. 3 | Test Ex. 4 | Test Ex. 5 |
|---|---|---|---|---|---|
| A. Aqueous phase | | | | | |
| Ion exchange water | Balance | Balance | Balance | Balance | Balance |
| Alkyl-modified carboxyvinyl polymer (Pemulen TR-2) | 0.1 | 0.1 | 0.1 | 0.1 | 0.1 |
| KOH | 0.05 | 0.05 | 0.05 | 0.05 | 0.05 |
| Hydroxypropylated β-cyclodextrin | 0.5 | 0.5 | 0.5 | 0.5 | 0.5 |
| Glycerol | 5.0 | 5.0 | 5.0 | 5.0 | 5.0 |
| Dipropylene glycol | 5.0 | 5.0 | 5.0 | 5.0 | 5.0 |
| B. Alcohol phase | | | | | |
| Ethyl alcohol | 10.0 | 10.0 | 10.0 | 10.0 | 10.0 |
| Methylparaben | 0.1 | 0.1 | 0.1 | 0.1 | 0.1 |
| Tocopherol acetate | 0.1 | 0.05 | 0.01 | 0.005 | 0.001 |
| Turbidity (%) | 98 | 75 | 23 | 12 | 7 |
| Stability after preparation | × | Δ | ○ | ○ | ○ |
| Stability after one month | × | Δ | ⊙ | ⊙ | ⊙ |

From the results of Table 1, it was learned that when the ingredient difficult to be dissolved in water, that is, the tocopherol acetate, and the alkyl-modified carboxyvinyl polymer, are formulated in a ratio of the alkyl-modified carboxyvinyl polymer by weight (ingredient insoluble in water:alkyl-modified carboxyvinyl polymer) of at least 1:10 (in other words the amount of the alkyl-modified carboxyvinyl polymer is at least 10 times by weight in excess of the amount of the ingredient difficult to be dissolved in water), the clarity and stability of the test product (stability immediately after preparation and stability over time) are particularly superior.

As opposed to this, it was learned that, when the amount of the tocopherol acetate formulated with respect to the alkyl-modified carboxyvinyl polymer is greater than this, there is a strong tendency for the stability of the test product to become inferior in both the short term and the long term and further for the clarity to become inferior.

That is, to sufficiently exhibit the effect desired in the present invention, it was learned that it is preferable to blend a certain degree of excess of alkyl-modified carboxyvinyl polymer with respect to the ingredient difficult to be dissolved in water (at least 10 times in ratio by weight of the ingredient difficult to be dissolved in water).

Test Examples 6 to 11

The cosmetic waters of the formulations shown in Table 2 were prepared by the same process as the cosmetic waters of the Test Examples listed in Table 1 and were evaluated as to the turbidity, stability over time, and safety of the cosmetic waters.

TABLE 2

| Ingredient | Test Ex. 6 | Test Ex. 7 | Test Ex. 8 | Test Ex. 9 | Test Ex. 10 | Test Ex. 11 |
|---|---|---|---|---|---|---|
| A. Aqueous phase | | | | | | |
| Ion exchange water | Balance | Balance | Balance | Balance | Balance | Balance |
| Alkyl-modified carboxyvinyl polymer (Pemulen TR-2) | 0.1 | 0.1 | 0.1 | 0.1 | 0.1 | 0.1 |
| KOH | 0.05 | 0.05 | 0.05 | 0.05 | 0.05 | 0.05 |
| Hydroxypropylated β-cyclodextrin | 0.0001 | 0.001 | 0.01 | 0.5 | 1.0 | 5.0 |
| Glycerol | 5.0 | 5.0 | 5.0 | 5.0 | 5.0 | 5.0 |
| Dipropylene glycol | 5.0 | 5.0 | 5.0 | 5.0 | 5.0 | 5.0 |
| B. Alcohol phase | | | | | | |
| Ethyl alcohol | 10.0 | 10.0 | 10.0 | 10.0 | 10.0 | 10.0 |
| Methylparaben | 0.1 | 0.1 | 0.1 | 0.1 | 0.1 | 0.1 |
| Tocopherol acetate | 0.01 | 0.01 | 6.01 | 0.01 | 0.01 | 0.01 |
| Perfume | 0.01 | 0.01 | 0.01 | 0.01 | 0.01 | 0.01 |
| Turbidity (%) | 45 | 18 | 10 | 6 | 5 | 5 |
| Stability after one month | × | ○ | ⊙ | ⊙ | ⊙ | Δ |
| Usability | ○ | ○ | ○ | ○ | ○ | × |

From the results of Table 2, it became clear that to sufficiently exhibit the effect desired in the present invention, it is preferable to formulate hydroxyalkylated cyclodextrin in an amount of at least 0.001% by weight of the cosmetic composition as a whole, particularly preferably at least 0.01% by weight.

However, it was also learned that, if hydrox-alkylated cyclodextrin is formulated in an amount of 5.0% by weight of the cosmetic composition as a whole, the stability over time conversely declines and there is an accompanying sticky feeling in use, and therefor, this is not desirable.

Test Examples 12 to 15

The cosmetic waters shown in Table 3 were prepared by adding the aqueous phases to the alcohol phases and then evaluated by the above-mentioned means as to the turbidity of the cosmetic waters, the stability over time, and the usability.

TABLE 3

| Ingredient | Test Ex. 12 | Test Ex. 13 | Test Ex. 14 | Test Ex. 15 |
|---|---|---|---|---|
| A. Aqueous phase | | | | |
| Ion exchange water | Balance | Balance | Balance | Balance |
| Alkyl-modified carboxyvinyl polymer (Pemulen TR-2) | 0.1 | 0.1 | — | 1.5 |
| KOH | 0.05 | 0.05 | — | 0.05 |
| Hydroxypropylated β-cyclodextrin | 0.5 | — | 0.5 | 0.5 |
| Glycerol | 5.0 | 5.0 | 5.0 | 5.0 |
| Dipropylene glycol | 5.0 | 5.0 | 5.0 | 5.0 |
| B. Alcohol phase | | | | |
| Ethyl alcohol | 10.0 | 10.0 | 10.0 | 10.0 |
| Methylparaben | 0.1 | 0.1 | 0.1 | 0.1 |
| Tocopherol acetate | 0.005 | 0.005 | 0.005 | 0.005 |
| Perfume | 0.005 | 0.005 | 0.005 | 0.005 |
| Turbidity (%) | 6 | 45 | 78 | 2 |
| Stability after one month | ⊙ | Δ | Δ | ○ |
| Usability | ○ | ○ | ○ | × |

From the results of Table 3, it became clear that the cosmetic water of Test Example 1 was a cosmetic water which was low in turbidity, excellent in long term stability over time, and showed little stickiness and that the effect desired in the present invention was sufficiently exhibited.

As opposed to this, it became clear that the cosmetic water of Test Example 13 or Test Example 14 not containing the alkyl-modified carboxyvinyl polymer or hydroxypropylated cyclodextrin exhibited a decline in turbidity and did not satisfy the effect desired in the present invention in terms of the clarity.

That is, it became clear that to obtain the effect desired by the present invention, it is necessary to formulate into the solubilized cosmetic composition both of the alkyl-modified carboxyvinyl polymer and hydroxypropylated cyclodextrin.

Further, the cosmetic water of Test Example 15 containing an excess of the alkyl-modified carboxyvinyl polymer was superior in clarity, but had an accompanying sticky feeling in use, therefore, could not exhibit the effect desired in the present invention in terms of the usability.

Example 1

Lotion

Cosmetic water of the formulation shown below was prepared by adding the alcohol phase to the aqueous phase. The cosmetic water was evaluated using the above means as well, and as a result, it was found that it was a cosmetic water with a low turbidity, excellent short term and long term stability, and no accompanying sticky feeling of use.

| Ingredients | Content (wt %) |
|---|---|
| A. Aqueous Phase | |
| Ion exchange water | Balance |
| Polyethylene glycol 4000 | 2.0 |
| 1,3-butylene glycol | 3.0 |
| Dipropylene glycol | 5.0 |
| Hydroxypropylated β-CD | 0.1 |
| Citric acid | 0.1 |
| Sodium citrate | 0.3 |
| Sodium metaphosphate | 0.1 |
| Sodium hyaluronate | 0.05 |
| Tranexamic acid | 0.5 |
| Albutin | 5.0 |
| Magnesium ascorbic acid phosphate | 1.0 |

| Ingredients | Content (wt %) |
|---|---|
| Aloe extract | 0.3 |
| Ginseng extract | 0.1 |
| Alkyl-modified carboxyvinyl polymer (Pemulen TR-1) | 0.3 |
| KOH | 0.2 |
| B. Alcohol Phase | |
| Ethyl alcohol | 12.0 |
| Methylparaben | 0.1 |
| Phenoxyethanol | 0.3 |
| Photosensitizing Dye No. 201 | 0.005 |
| 2-ethylhexyl p-oxycinnamate | 0.2 |
| Vitamin A palmitate | 0.03 |
| Perfume | 0.01 |

Example 2

Hair Tonic Composition

A hair tonic composition of the formulation shown below was prepared by adding the alcohol phase in the aqueous phase. The hair tonic composition was evaluated using the above means as well, whereupon it was found that it was a hair tonic with a low turbidity, excellent short term and long term stability, and no accompanying sticky feeling of use.

| Ingredients | Content (wt %) |
|---|---|
| A. Aqueous Phase | |
| Ion exchange water | Balance |
| Glycerol | 2.0 |
| Lactic acid | 0.01 |
| Sodium lactate | 0.5 |
| Trisodium edetate | 0.03 |
| Tranexamic acid | 2.5 |
| Allantoin | 0.1 |
| Zinc paraphenol sulfonate | 0.3 |
| Hydroxyethylated β-CD | 0.5 |
| Hydroxypropylated β-CD | 0.5 |
| dl-α-tocopherol 2-L-ascorbate phosphate diester potassium salt | 0.1 |
| Monoammonium glycyrrhizinate | 0.02 |
| Alkyl-modified carboxyvinyl polymer (Carbopol 1342) | 0.5 |
| KOH | 0.3 |
| B. Alcohol Phase | |
| Ethanol | 55.0 |
| Oxybenzone | 0.4 |
| dl-α-tocopherol | 0.03 |
| Stearyl glycyrrhizinate | 0.02 |
| d-Camphor | 0.5 |
| perfume | 0.1 |

Example 3

Clear Essence

A clear essence of the formulation shown below was prepared by stirring and dissolving the aqueous phase and then adding the alcohol phase therein. The clear essence was evaluated using the above means as well, whereupon it was found that it was a clear essence with a low turbidity, excellent short term and long term stability, and no accompanying sticky feeling of use.

| Ingredients | Content (wt %) |
|---|---|
| A. Aqueous Phase | |
| Ion exchange water | Balance |
| Polyethylene glycol 400 | 5.0 |
| Propylene glycol | 5.0 |
| Dipotassium glycyrrhinizate | 0.1 |
| Glycolic acid | 2.0 |
| L-ascorbate-2-glycoxide | 3.0 |
| Hydroxypropylated α-CD | 1.0 |
| Hydroxypropylated β-CD | 1.0 |
| Hydroxypropylated γ-CD | 1.0 |
| Carboxyvinyl polymer | 0.5 |
| Alkyl-modified carboxyvinyl polymer (Pemulen TR-2) | 0.005 |
| KOH | 0.2 |
| Sodium hydroxymethoxybenzophenone sulfonate | 0.1 |
| B. Alcohol Phase | |
| Ethanol | 10.0 |
| 4-tert-butyl-4'-methoxy dibenzoyl methane | 0.05 |
| Tocopherol acetate | 0.0005 |
| Methylparaben | 0.1 |
| Perfume | 0.03 |

INDUSTRIAL APPLICABILITY

As explained above, according to the present invention, there is provided a solubilized cosmetic composition exhibiting long term stability over time in a soluble state, improved in feeling in use, and superior in clarity.

What is claimed is:

1. A solubilized cosmetic composition comprising (i) a pharmaceutically active agent or a cosmetic agent which is difficult to be dissolved in water, (ii) an acrylate-methacrylate alkyl copolymer and (iii) 0.001% by weight to 5.0% by weight of the cosmetic composition, of a hydroxyalkylated cyclodextrin so as to solubilize said pharmaceutically active agent or said cosmetic agent.

2. A solubilized cosmetic composition as claimed in claim 1, wherein the content of the acrylate-methacrylate alkyl copolymer is from 0.0001% by weight to 1.0% by weight, based upon the total weight of the cosmetic composition.

3. A solubilized cosmetic composition as claimed in claim 1, wherein the content of the acrylate-methacrylate alkyl copolymer is at least 10 times said pharmaceutically active agent or said cosmetic agent in terms of weight.

4. A solubilized cosmetic composition as claimed in claim 1, wherein the content of the hydroxyalkylated cyclodextrin if from 0.01% by weight to 1.0% by weight, based upon the total weight of the cosmetic composition.

* * * * *